(12) United States Patent
Yoshida et al.

(10) Patent No.: US 10,457,756 B2
(45) Date of Patent: Oct. 29, 2019

(54) FLUORINATED COMPOUND, CURABLE COMPOSITION AND CURED PRODUCT

(71) Applicant: AGC Inc., Chiyoda-ku (JP)

(72) Inventors: Jun Yoshida, Chiyoda-ku (JP); Keisuke Takagi, Chiyoda-ku (JP); Hidenobu Murofushi, Chiyoda-ku (JP); Tomoaki Sakurada, Chiyoda-ku (JP)

(73) Assignee: AGC Inc., Chiyoda-ku (JP)

( * ) Notice: Subject to any disclaimer, the term of this patent is extended or adjusted under 35 U.S.C. 154(b) by 4 days.

(21) Appl. No.: 15/818,095

(22) Filed: Nov. 20, 2017

(65) Prior Publication Data

US 2018/0072830 A1 Mar. 15, 2018

Related U.S. Application Data

(63) Continuation of application No. PCT/JP2016/072207, filed on Jul. 28, 2016.

(30) Foreign Application Priority Data

Jul. 30, 2015 (JP) .................................. 2015-150825
Oct. 6, 2015 (JP) .................................. 2015-198756

(51) Int. Cl.
| | | |
|---|---|---|
| C08F 122/22 | (2006.01) | |
| C07C 271/16 | (2006.01) | |
| C07C 323/12 | (2006.01) | |
| C07C 323/43 | (2006.01) | |
| C07D 303/28 | (2006.01) | |
| C08F 122/24 | (2006.01) | |
| C08G 59/30 | (2006.01) | |
| C08G 59/68 | (2006.01) | |
| C08G 59/04 | (2006.01) | |
| C08G 65/00 | (2006.01) | |
| C08G 65/331 | (2006.01) | |
| C08G 65/333 | (2006.01) | |
| C08G 65/334 | (2006.01) | |
| C08F 222/22 | (2006.01) | |

(52) U.S. Cl.
CPC .......... *C08F 122/22* (2013.01); *C07C 271/16* (2013.01); *C07C 323/12* (2013.01); *C07C 323/43* (2013.01); *C07D 303/28* (2013.01); *C08F 122/24* (2013.01); *C08G 59/04* (2013.01); *C08G 59/308* (2013.01); *C08G 59/687* (2013.01); *C08G 65/007* (2013.01); *C08G 65/3312* (2013.01); *C08G 65/3342* (2013.01); *C08G 65/33306* (2013.01); *C08G 65/33348* (2013.01); *C08F 2222/225* (2013.01)

(58) Field of Classification Search
CPC .......... C08F 20/22; C08F 20/26; C08F 20/34; C08F 120/26; C08F 122/22; C08F 122/24; C07C 323/42; C07C 323/43
See application file for complete search history.

(56) References Cited

U.S. PATENT DOCUMENTS

| | | | | | |
|---|---|---|---|---|---|
| 3,553,179 | A | * | 1/1971 | Bartlett | .................... C08F 20/34 524/544 |
| 8,476,385 | B2 | * | 7/2013 | Dams | .................... C08F 220/24 526/245 |
| 9,540,404 | B2 | * | 1/2017 | Murotani | .................. C09K 3/18 |
| 9,580,549 | B2 | * | 2/2017 | Murotani | .................. C07F 7/18 |
| 9,598,657 | B2 | * | 3/2017 | Isobe | .................. C08G 65/007 |
| 9,637,650 | B2 | * | 5/2017 | Murotani | ............. C09D 171/00 |
| 9,969,890 | B2 | * | 5/2018 | Takao | ...................... C09D 4/00 |
| 2009/0004098 | A1 | | 1/2009 | Schmidt et al. | |
| 2010/0304113 | A1 | | 12/2010 | Chang et al. | |
| 2011/0003130 | A1 | | 1/2011 | Marchet et al. | |
| 2012/0135206 | A1 | | 5/2012 | Haraguchi et al. | |
| 2013/0258467 | A1 | * | 10/2013 | Shiraiwa | ................ C09D 5/006 359/483.01 |
| 2014/0287246 | A1 | * | 9/2014 | Murotani | .................. C07F 7/18 428/446 |
| 2015/0315443 | A1 | * | 11/2015 | Takeda | .................... C03C 17/30 428/429 |
| 2015/0344703 | A1 | | 12/2015 | Takao et al. | |
| 2016/0137947 | A1 | | 5/2016 | Isobe et al. | |

FOREIGN PATENT DOCUMENTS

| | | |
|---|---|---|
| JP | 10-316406 | 12/1998 |
| JP | 2001-262011 | 9/2001 |
| JP | 2002-3550 | 1/2002 |
| JP | 2004-43285 | 2/2004 |
| JP | 2004-292282 | 10/2004 |
| JP | 2005-162781 | 6/2005 |
| JP | 2006-2132 | 1/2006 |
| JP | 2006-213748 | 8/2006 |
| JP | 2006-291077 | 10/2006 |
| JP | 2008-120605 | 5/2008 |
| JP | 2008-297400 | 12/2008 |
| JP | 2009-143974 | 7/2009 |
| JP | 2011-136857 | 7/2011 |
| JP | 2011-154396 | 8/2011 |

(Continued)

OTHER PUBLICATIONS

International Search Report dated Oct. 11, 2016 in PCT/JP2016/072207, filed on Jul. 28, 2016.

*Primary Examiner* — Nicole M. Buie-Hatcher
(74) *Attorney, Agent, or Firm* — Oblon, McClelland, Maier & Neustadt, L.L.P.

(57) ABSTRACT

To provide a fluorinated compound capable of obtaining a cured product which is excellent in heat resistance and mold release and has a high Abbe number; a curable composition containing such a compound; and a cured product which is excellent in heat resistance and mold release and has a high Abbe number. The fluorinated compound is represented by the following formula (A):

$$[Z\text{—}OCH_2CF_2CF_2CF_2OCFHCF_2\text{—}X\text{—}]_nQ \qquad (A)$$

where n is an integer of at least 1, Q is a n-valent organic group, X is —O—, —NH— or —S—, and Z is a group having at least one polymerizable functional group.

12 Claims, No Drawings

(56) References Cited

FOREIGN PATENT DOCUMENTS

| JP | 2012-52098 | 3/2012 | |
|---|---|---|---|
| JP | 5781384 | 9/2015 | |
| WO | WO-2010009296 A2 * | 1/2010 | ............ C07F 7/1804 |
| WO | WO 2012/137672 A1 | 10/2012 | |
| WO | WO-2013121985 A1 * | 8/2013 | ................ C07F 7/18 |
| WO | WO-2013121986 A1 * | 8/2013 | ............ C09D 171/00 |
| WO | WO-2014126064 A1 * | 8/2014 | ............. C03C 17/30 |
| WO | WO 2014/136787 A1 | 9/2014 | |
| WO | WO 2015/022871 A1 | 2/2015 | |

* cited by examiner

FLUORINATED COMPOUND, CURABLE COMPOSITION AND CURED PRODUCT

This application is a continuation of PCT Application No. PCT/JP2016/072207, filed on Jul. 28, 2016, which is based upon and claims the benefit of priority from Japanese Patent Application No. 2015-150825 filed on Jul. 30, 2015 and Japanese Patent Application No. 2015-198756 filed on Oct. 6, 2015. The contents of those applications are incorporated herein by reference in their entireties.

TECHNICAL FIELD

The present invention relates to a fluorinated compound, a curable composition containing the fluorinated compound, and a cured product obtained by curing the curable composition.

BACKGROUND ART

As a method of forming a fine pattern in a short time in the production of an optical member (such as a lens array, a prism, etc.), a method is known wherein a curable composition is cured in a such state that the curable composition is in contact with a mold having a reverse pattern of the fine pattern at its surface, to form a cured product having the fine pattern at its surface, and the cured product is used as an optical member.

As the curable composition for an optical member, the following one has, for example, been proposed.

A curable composition comprising a polyfunctional (meth)acrylate copolymer obtainable by copolymerizing components including a monofunctional (meth)acrylate having an alicyclic structure, a monofunctional (meth)acrylate having a hydroxy group, a bifunctional (meth)acrylate and 2,4-diphenyl-4-methyl-1-pentene, and a compound having at least one polymerizable carbon-carbon double bond (Patent Document 1).

PRIOR ART DOCUMENT

Patent Document

Patent Document 1: JP-A-2012-052098

DISCLOSURE OF INVENTION

Technical Problem

However, the curable composition described in Patent Document 1 has the following problems.
 When the cured product is heated for a long time, it tends to be colored and thus is poor in heat resistance.
 After curing the curable composition in a state of being in contact with a mold, the cured product is hardly separable from the mold and thus is poor in mold release.
 Since the Abbe number of the cured product is low, when it is used in combination with a glass substrate, chromatic aberration occurs.

The present invention is to provide a fluorinated compound and a curable composition capable of obtaining a cured product which is excellent in heat resistance and mold release and has a high Abbe number, as well as a cured product which is excellent in heat resistance and mold release and has a high Abbe number.

Solution to Problem

The present invention has the following constructions.

[1] A fluorinated compound represented by the following formula (A):

[Z—OCH$_2$CF$_2$CF$_2$CF$_2$OCFHCF$_2$—X-]$_n$Q  (A)

where n is an integer of at least 1, Q is a n-valent organic group, X is —O—, —NH— or —S—, and Z is a group having at least one polymerizable functional group.

[2] The fluorinated compound according to [1], wherein n is an integer of from 2 to 6.

[3] The fluorinated compound according to [1] or [2], wherein Q is a n-valent hydrocarbon group, or a group having at least one etheric oxygen atom between carbon atoms in an n-valent hydrocarbon group.

[4] The fluorinated compound according to [3], wherein the number of carbon atoms in Q is from 2 to 24, and in a case where Q has etheric oxygen atom(s) between carbon atoms, the number of such etheric oxygen atom(s) is 1 or 2.

[5] The fluorinated compound according to any one of [1] to [4], wherein X is —O—.

[6] The fluorinated compound according to any one of [1] to [5], wherein the polymerizable functional group is a group having a polymerizable carbon-carbon double bond, or an epoxy group.

[7] The fluorinated compound according to [6], wherein the group having a polymerizable carbon-carbon double bond is a (meth)acryloyl group.

[8] The fluorinated compound according to any one of [1] to [7], wherein Z has —NHC(O)— at the end on the side bonded to the oxygen atom adjacent to Z (provided that the carbon atom in the —NHC(O)— is bonded to the oxygen atom adjacent to Z).

[9] The fluorinated compound according to any one of [1] to [5], wherein Z is a group represented by the following formula (g1), a group represented by the following formula (g2), or a group represented by the following formula (g3):

CH$_2$=C(R)—C(O)O—R$^1$—NHC(O)—  (g1)

{CH$_2$=C(R)—C(O)O—}$_2$R$^2$—NHC(O)—  (g2)

CH$_2$=C(R)—C(O)O—R$^3$—CH(OH)—CH$_2$—  (g3)

Ep-R$^4$—  (g4)

where R is a hydrogen atom or a methyl group, R$^1$ is a C$_{1-6}$ alkylene group, or a group having at least one etheric oxygen atom between carbon atoms in a C$_{2-6}$ alkylene group, R$^2$ is a C$_{1-4}$ alkanetriyl group, or a group having at least one etheric oxygen atom between carbon atoms in a C$_{2-4}$ alkanetriyl group, R$^3$ is a C$_{1-5}$ alkylene group, or a group having at least one etheric oxygen atom between carbon atoms in a C$_{2-5}$ alkylene group, R$^4$ is a C$_{1-5}$ alkylene group, or a group having at least one etheric oxygen atom between carbon atoms in a C$_{2-5}$ alkylene group, and Ep is an epoxy group.

[10] A curable composition comprising at least one fluorinated compound as defined in any one of [1] to [9], and a polymerization initiator.

[11] The curable composition according to [10], which further contains a compound having at least one polymerizable functional group (but excluding the fluorinated compound).

[12] The curable composition according to [10] or [11], wherein the polymerization initiator is a photopolymerization initiator.

[13] A cured product obtained by curing the curable composition as defined in any one of [10] to [12].

Advantageous Effects of Invention

According to the fluorinated compound and the curable composition of the present invention, it is possible to obtain a cured product which is excellent in heat resistance and mold release and has a high Abbe number.

The cured product of the present invention is excellent in heat resistance and mold release and has a high Abbe number.

DESCRIPTION OF EMBODIMENTS

In this specification, a compound represented by the formula (1) will also be referred to as a compound (1). Compounds represented by other formulae will also be referred to in the same manner.

In this specification, a group represented by the formula (g1) will also be referred to as a group (g1). Groups represented by other formulae will also be referred to in the same manner.

In this specification, the meanings of the following terms are as follows.

A "polymerizable functional group" means a group capable of radical polymerization or cationic polymerization.

A "(meth)acryloyl group" is a general term for an acryloyl group and a methacryloyl group.

A "(meth) acrylate" is a general term for an acrylate and a methacrylate.

A "(meth)acrylamide" is a general term for an acrylamide and a methacrylamide.

<Fluorinated Compound>

A fluorinated compound of the present invention (hereinafter referred to also as a "compound (A)") is a compound represented by the following formula (A).

$$[Z-OCH_2CF_2CF_2CF_2OCFHCF_2-X-]_nQ \quad (A)$$

n is an integer of at least 1. As n, at least 2 is preferred from such a viewpoint that it is thereby possible to increase the viscosity of the curable composition, and the cured product will be excellent in heat resistance, mechanical strength, etc., and from 2 to 6 is more preferred, and from 2 to 4 is further preferred, from the viewpoint of production efficiency of the compounds (A) and handling efficiency of the compound (A).

Q is an n-valent organic group. As Q, from the viewpoint of availability of raw material and costs, a n-valent hydrocarbon group, or a group having at least one etheric oxygen atom between carbon atoms in a n-valent hydrocarbon group, is preferred, and a n-valent hydrocarbon group is particularly preferred. The number of etheric oxygen atoms is preferably from 1 to 3, more preferably 1 or 2.

The number of carbon atoms in Q is preferably from 2 to 24, more preferably from 2 to 12, further preferably from 2 to 5, from the viewpoint of availability of raw material, production efficiency of the compound (A) and the Abbe number.

Monovalent Q may be an alkyl group, or an alkyl group having an etheric oxygen atom between carbon atoms. The number of carbon atoms in monovalent Q is preferably from 1 to 8. Specifically, for example, $CH_3 CH_2$—, $CH_3 CH_2 CH_2$—, $CH_3 CH_2 CH_2 CH_2$—, $CH_3 OCH_2 CH_2$—, $CH_3 CH_2 OCH_2 CH_2$—, etc. may be mentioned.

Divalent Q may be an alkylene group, or an alkylene group having an etheric oxygen atom between carbon atoms. The number of carbon atoms in divalent Q is preferably from 2 to 12. Specifically, for example, —$CH_2 CH_2$—, —$CH_2 CH_2 CH_2$—, —$CH_2CH_2CH_2CH_2$—, —$CH_2CH_2CH_2CH_2CH_2$—, —$CH_2CH_2CH_2CH_2CH_2 CH_2$—, —$CH_2 C(CH_3)_2 CH_2$—, —$C(CH_3)_2 CH_2 CH_2 C(CH_3)_2$—, —$CH_2 CH_2 OCH_2 CH_2$—, —$CH_2 CH_2 CH_2 OCH_2 CH_2 CH_2$—, —$CH(CH_3)CH_2 OCH_2 CH(CH_3)$—, etc. may be mentioned.

Trivalent or higher valent Q may be a tri- to hexa-valent hydrocarbon group, or a tri- to hexa-valent hydrocarbon group having an etheric oxygen atom between carbon atoms. The number of carbon atoms in the trivalent or higher valent Q is preferably from 3 to 12. Specifically, the following groups, may, for example, be mentioned.

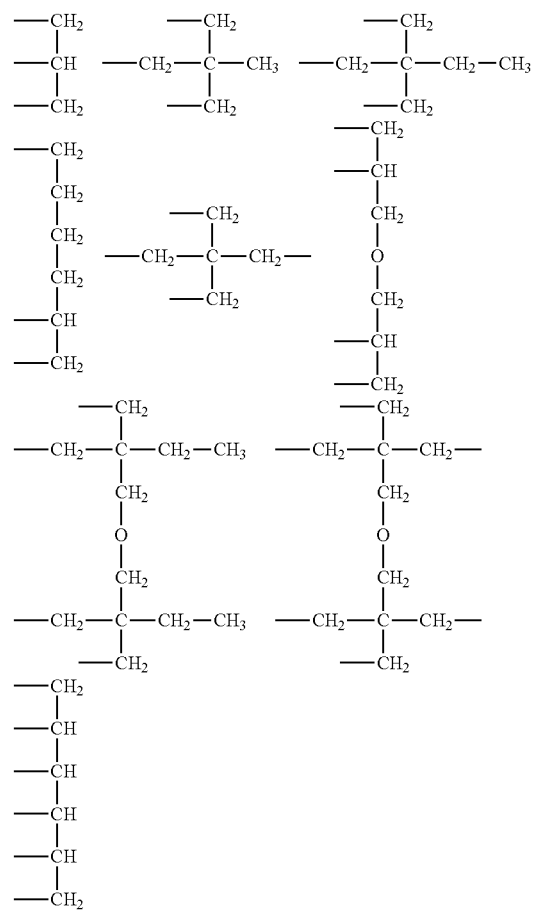

X is —O—, —NH— or —S—. As X, —O— is preferred from the viewpoint of production efficiency of the compound (A).

Z is a group having at least one polymerizable functional group.

The number of polymerizable functional groups in one Z is preferably 1 or 2, from the viewpoint of availability of raw material and production efficiency of the compound (A).

The polymerizable functional group may be a group capable of radical polymerization, or a group capable of cationic polymerization. As the polymerizable functional group, a group capable of radical polymerization is preferred from such a viewpoint that a curable product can thereby be easily produced at a relatively low temperature in a short time.

As the group capable of radical polymerization, a group having a polymerizable carbon-carbon double bond may be mentioned.

The group having a polymerizable carbon-carbon double bond may, for example, be a (meth)acryloyl group, a vinyl group, an allyl group, an isopropenyl group, a 3-butenyl group, a trifluorovinyl group, etc. As the group capable of radical polymerization, from the viewpoint of excellent curability, a (meth)acryloyl group is preferred, and an acryloyl group is more preferred.

The group capable of cation polymerization may be a group having a cyclic ether having a ring-opening reactivity. The cyclic ether group having a ring-opening reactivity may, for example, be an epoxy group, an oxetanyl group, etc., and an epoxy group is preferred.

As Z, from such a viewpoint that the viscosity of the curable composition becomes high, and the moldability will be excellent, one having —NHC(O)— or —CH(OH)—CH$_2$— at the end on the side bonded to the oxygen atom adjacent to Z, is preferred, and one having —NHC(O)— is more preferred. Here, the carbon atom in —NHC(O)— or the carbon atom of CH$_2$ in —CH(OH)—CH$_2$—, is bonded to the oxygen atom adjacent to Z.

As Z, from such a viewpoint that a cured product can be easily produced by photocuring, and further from the viewpoint of availability of raw material and efficient production of the compound (A), group (g1), group (g2), group (g3) or group (g4) is preferred, and from such a viewpoint that the viscosity of the curable composition becomes high, and the moldability will be excellent, group (g1) or group (g2) is more preferred.

CH$_2$=C(R)—C(O)O—R$^1$—NHC(O)—     (g1)

{CH$_2$=C(R)—C(O)O—}$_2$R$^2$—NHC(O)—     (g2)

CH$_2$=C(R)—C(O)O—R$^3$—CH(OH)—CH$_2$—     (g3)

Ep-R$^4$—     (g4)

where R is a hydrogen atom or a methyl group, R$^1$ is a C$_{1-6}$ alkylene group, or a group having at least one etheric oxygen atom between carbon atoms in a C$_{2-6}$ alkylene group, R$^2$ is C$_{1-4}$ alkanetriyl group, or a group having at least one etheric oxygen atom between carbon atoms in a C$_{2-4}$ alkanetriyl group, R$^3$ is a C$_{1-5}$ alkylene group, or a group having at least one etheric oxygen atom between carbon atoms in a C$_{2-5}$ alkylene group, R$^4$ is a C$_{1-5}$ alkylene group, or a group having at least one etheric oxygen atom between carbon atoms in a C$_{2-5}$ alkylene group, and Ep is an epoxy group.

As group (g1) and group (g3), for example, the following groups may be mentioned.

CH$_2$=CH—C(O)O—CH$_2$CH$_2$—NHC(O)—,

CH$_2$=C(CH$_3$)—C(O)O—CH$_2$CH$_2$—NHC(O)—,

CH$_2$=CH—C(O)O—CH$_2$CH$_2$OCH$_2$CH$_2$—NHC(O)—,

CH$_2$=C(CH$_3$)—C(O)O—CH$_2$CH$_2$OCH$_2$CH$_2$—NHC(O)—,

CH$_2$=CH—C(O)O—CH$_2$—CH(OH)—CH$_2$—,

CH$_2$=C(CH$_3$)—C(O)O—CH$_2$—CH(OH)—CH$_2$—,

CH$_2$=CH—C(O)O—(CH$_2$)$_4$OCH$_2$—CH(OH)—CH$_2$—,

CH$_2$=C(CH$_3$)—C(O)O—(CH$_2$)$_4$OCH$_2$—CH(OH)—CH$_2$—.

As group (g2), for example, the following groups may be mentioned.

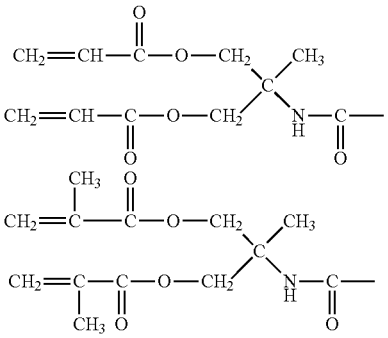

As group (g4), for example, the following group may be mentioned.

Ep-CH$_2$—.

In the compound (A), —OCH$_2$CF$_2$CF$_2$CF$_2$OCFHCF$_2$— is a structure derived from a compound (2) being a raw material for the compound (A) which will be described later. Since the compound (A) has such a structure, it is possible to obtain a cured product which is excellent in heat resistance and mold release and has a high Abbe number. Further, since such a structure has hydrogen atoms, as compared with a structure having hydrogen atoms all replaced by fluorine atoms, compatibility between the compound (A) and other components will be good.

The fluorine content in the compound (A) is preferably at least 25 mass %, more preferably at least 30 mass %, further preferably at least 35 mass %. When the fluorine content of the compound (A) is at least the lower limit value in the above range, heat resistance and mold release of the cured product will be further excellent, and the Abbe number of the cured product will be higher.

The viscosity of the compound (A) is preferably from 500 to 10,000 mPa·s, more preferably from 1,000 to 5,000 mPa·s, further preferably from 1,000 to 2,000 mPa·s. When the viscosity of the compound (A) is at least the lower limit value in the above range, the viscosity of the curable composition becomes high, and moldability will be excellent. When the viscosity of the compound (A) is at most the upper limit value in the above range, the compound (A) will be easy in handling.

The refractive index of the compound (A) to light with a wavelength of 589 nm is preferably less than 1.42, more preferably less than 1.40. When the refractive index is at most the upper limit value in the above range, it is possible to sufficiently reduce reflection at the interface between the cured product of the compound (A) and the air. The lower limit value of the refractive index of the compound (A) to light with a wavelength of 589 nm is 1.32.

The Abbe number obtained from the following formula (I) of the compound (A) is preferably at least 55, more preferably at least 60. When the Abbe number is at least the lower limit value in the above range, in a case where the cured product and a glass substrate are used in combination, chromatic aberration is less likely to occur. The higher the Abbe number, the better, and the upper limit value is not particularly limited, but is about 70 when considering that it is an organic substance.

$$\nu_D = (n_D - 1)/(n_F - n_C) \quad (I)$$

where $v_D$ is the Abbe number, $n_D$ is the refractive index to light with a wavelength of 589 nm, $n_F$ is the refractive index to light with a wavelength of 486 nm, and $n_C$ is the refractive index to light with a wavelength of 656 nm.

(Method for Producing Compound (A))

The compound (A) can be produced, for example, by a method having the following steps (i) to (iii).

Step (i):

A compound (1) is reduced with a reducing agent (such as sodium borohydride) to obtain a compound (2).

$$CH_3OC(O)CF_2CF_2CF_2OCF{=}CF_2 \qquad (1)$$

$$HOCH_2CF_2CF_2CF_2OCF{=}CF_2 \qquad (2)$$

Step (ii):

In the presence of a basic compound (such as potassium carbonate), a compound (3) is addition-reacted to the compound (2) to obtain a compound (4).

$$HOCH_2CF_2CF_2CF_2OCF{=}CF_2 \qquad (2)$$

$$[HX\text{-}]_nQ \qquad (3)$$

$$[HOCH_2CF_2CF_2CF_2OCFHCF_2\text{---}X\text{-}]_nQ \qquad (4)$$

where n, Q and X are as described above, and the preferred modes are also the same.

The compound (3) wherein X is —O— and n is 1, may, for example, be methanol, ethanol, butanol etc.

The compound (3) wherein X is —O— and n is 2, may, for example, be ethylene glycol, propylene glycol, 1,4-butanediol, 1,5-pentanediol, 1,6-hexanediol, 2,2-dimethyl-1,3-propanediol, 2,5-dimethyl-2,5-hexanediol, diethylene glycol, dipropylene glycol, etc.

The compound (3) wherein X is —O— and n is 3, may, for example, be glycerin, trimethylol ethane, trimethylol propane, 1,2,6-hexanetriol, etc.

The compound (3) wherein X is —O— and n is the 4, may, for example, be diglycerin, pentaerythritol, ditrimethylolpropane, etc.

The compound (3) wherein X is —O— and n is 6, may, for example, be dipentaerythritol, sorbitol, mannitol, dulcitol, etc.

The compound (3) wherein X is —NH—, may, for example, be ethylenediamine, hexamethylenediamine, 1,4-cyclohexane diamine, 1,2,3-propane triamine, 1,6,11-undecane triamine, etc.

The compound (3) wherein X is —S—, may, for example, be 1,2-ethanedithiol, 1,3-propanedithiol, 1,6-hexanedithiol, ethane-1,1,1-trithiol, 1,4-cyclohexanedithiol, 2,5-dimercaptomethyl-1,4-dithiane, thiocyanuric acid, etc.

Step (iii):

In a case where Z is group (g1), the compound (4) and a compound (5) are reacted in the presence of a urethane catalyst (such as dibutyltin dilaurate) to obtain a compound (A1). The compound (5) may be an acryloyloxy alkyl isocyanate such as 2-acryloyloxyethyl isocyanate.

$$[HOCH_2CF_2CF_2CF_2OCFHCF_2\text{---}X\text{-}]_nQ \qquad (4)$$

$$CH_2{=}C(R)\text{---}C(O)O\text{---}R^1\text{---}NCO \qquad (5)$$

$$[CH_2{=}C(R)\text{---}C(O)O\text{---}R^1\text{---}NHC(O)\text{---} \\ OCH_2CF_2CF_2CF_2OCFHCF_2\text{---}X\text{-}]_nQ \qquad (A1)$$

where n, Q, X, R and $R^1$ are as described above, and the preferred modes are also the same.

In a case where Z is group (g2), the compound (4) and a compound (6) are reacted in the presence of a urethane catalyst (such as dibutyltin dilaurate), to obtain a compound (A2). The compound (6) may be 1,1-(bis acryloyloxymethyl)ethyl isocyanate.

$$[HOCH_2CF_2CF_2CF_2OCFHCF_2\text{---}X\text{-}]_nQ \qquad (4)$$

$$\{CH_2{=}C(R)\text{---}C(O)O\text{---}\}_2R^2\text{---}NCO \qquad (6)$$

$$[\{CH_2{=}C(R)\text{---}C(O)O\text{---}\}_2R^2\text{---}NHC(O)\text{---} \\ OCH_2CF_2CF_2CF_2OCFHCF_2\text{---}X\text{-}]_nQ \qquad (A2)$$

where n, Q, X, R and $R^2$ are as described above, and the preferred modes are also the same.

In a case where Z is group (g3), the compound (4) and a compound (7) are reacted to obtain a compound (A3). The compound (7) may, for example, be glycidyl acrylate.

$$[HOCH_2CF_2CF_2CF_2OCFHCF_2\text{---}X\text{-}]_nQ \qquad (4)$$

$$CH_2{=}C(R)\text{---}C(O)O\text{---}R^3Ep \qquad (7)$$

$$[CH_2{=}C(R)\text{---}C(O)O\text{---}R^3\text{---}CH(OH)\text{---}CH_2\text{---} \\ OCH_2CF_2CF_2CF_2OCFHCF_2\text{---}X\text{-}]nQ \qquad (A3)$$

where n, Q, X, R and $R^3$ are as described above, and the preferred modes are also the same. Ep is an epoxy group.

In a case where Z is group (g4), the compound (4) and a compound (8) are reacted to obtain a compound (A4). The compound (8) may, for example, be epichlorohydrin.

$$[HOCH_2CF_2CF_2CF_2OCFHCF_2\text{---}X\text{-}]_nQ \qquad (4)$$

$$Ep\text{-}R^4\text{---}Y \qquad (8)$$

$$[Ep\text{-}R^4\text{---}OCH_2CF_2CF_2CF_2OCFHCF_2\text{---}X\text{-}]_nQ \qquad (A4)$$

where n, Q, X, $R^4$ and Ep are as described above, and the preferred modes are also the same. Y is a halogen group.

(Advantageous Effects)

The compound (A) as described above, has a structure of —OCH$_2$ CF$_2$ CF$_2$ CF$_2$ OCFHCF$_2$—, whereby it is possible, by curing a curable composition containing the compound (A), to obtain a cured product which is excellent in heat resistance and mold release and has a high Abbe number.

<Curable Composition>

The curable composition of the present invention comprises the compound (A) and a polymerization initiator, as essential components.

The curable composition of the present invention may contain, as the case requires, a compound having at least one polymerizable functional group other than the compound (A), additives, etc. A compound having at least one curable functional group other than the compound (A), will be hereinafter referred to as a "compound (C)".

(Compound (A))

As the compound (A), one type may be used alone, or two or more types may be used in combination.

At the time of producing the compound (A), if a compound of $[HX\text{-}]_nQ$ wherein n is at least 2, is used as the compound (3), a compound wherein some of HX— are unreacted, may sometimes be formed. Therefore, there may be a case where the resulting product becomes a mixture of a plurality of compounds (A) which are different from one another in the number of [Z—OCH$_2$ CF$_2$ CF$_2$ CF$_2$ OCF-HCF$_2$—X—]. If such a mixture is used for the preparation of a curable composition without purification, the resulting composition will contain a plurality of compounds (A).

(Polymerization Initiator)

The polymerization initiator is suitably selected for use depending upon the type of the polymerizable functional group in Z of the compound (A), the curing method (photocuring or thermosetting), etc.

The polymerization initiator may be a photopolymerization initiator or a thermal polymerization initiator. As the polymerization initiator, from the viewpoint of production efficiency of a cured product, a photopolymerization initiator is preferred.

The photopolymerization initiator may be a photoradical polymerization initiator which generates radicals by absorbing light, a photocationic photopolymerization initiator which generates cations by absorbing light, etc. As the photopolymerization initiator, from the viewpoint of production efficiency of a cured product, a photoradical polymerization initiator is preferred.

The photoradical polymerization initiator may, for example, be an alkylphenone-type photopolymerization initiator, an acylphosphine oxide-type photopolymerization initiator, a titanocene-type photopolymerization initiator, an oxime ester-type photopolymerization initiator, an oxyphenyl acid ester-type photopolymerization initiator, a benzoin-type photopolymerization initiator, a benzophenone-type photopolymerization initiator, a thioxanthone-type photopolymerization initiator, a benzyl-(o-ethoxycarbonyl)-α-monooxime, a glyoxy ester, 3-ketocoumarin, 2-ethyl anthraquinone, camphorquinone, tetramethylthiuram sulfide, azobisisobutyronitrile, benzoyl peroxide, a dialkyl peroxide, tert-butyl peroxypivalate, etc. From the viewpoint of sensitivity and compatibility, an alkyl phenone-type photopolymerization initiator, an acylphosphine oxide-type photopolymerization initiator, a benzoin-type photopolymerization initiator or a benzophenone-type photopolymerization initiator, is preferred.

The photocationic polymerization initiator may, for example, be a photo-acid generator for generating cations (acid) by receiving radiation of light.

The photo-acid generator may, for example, be a sulfonium salt, an iodonium salt, a phosphonium salt, etc.

As the photopolymerization initiator, one type may be used alone, or two or more types may be used in combination.

The thermal polymerization initiator may, for example, be 2,2'-azobisisobutyronitrile, benzoyl peroxide, tert-butyl hydroperoxide, cumene hydroperoxide, di-tert-butyl peroxide, dicumyl peroxide, etc. In view of the decomposition temperature, 2,2'-azobisisobutyronitrile or benzoyl peroxide is preferred.

As the thermal polymerization initiator, one type may be used alone, or two or more types may be used in combination.

(Compound (C))

The polymerizable functional group of the compound (C), is a group capable of radical polymerization when the polymerizable functional group of the compound (A) is a group capable of radical polymerization, or a group capable of cationic polymerization when the polymerizable functional group of the compound (A) is a group capable of cationic polymerization. The polymerizable functional group of the compound (C) is preferably a (meth)acryloyl group from the viewpoint of polymerizability of the compound (C) one another or from the viewpoint of copolymerizability between the compound (A) and the compound (C).

The compound (C) is a component to dissolve other components or to improve the sensitivity of the curable composition. In particular, it has an effect to improve compatibility of the respective components. When compatibility of the respective components is good, foaming during preparation of the curable composition will be suppressed, and filtering will be facilitated, whereby it becomes easy to prepare the curable composition and a uniform curable composition will be obtained. Further, a homogeneous cured product is obtainable, whereby mold release and mechanical strength will be sufficiently exhibited. Further, depending on the type of the compound (C), it is possible to adjust various physical properties such as dry etching resistance, wet etching resistance, transparency, viscosity, refractive index, hardness, mechanical strength, flexibility, adhesion to a substrate, etc., of the cured product of the curable composition.

As the compound (C), a compound (C) having a fluorine atom and at least one polymerizable functional group, or a compound (C) having no fluorine atom and having at least one polymerizable functional group, may be mentioned.

As the compound (C) having a fluorine atom, wherein the polymerizable functional group is a group capable of radical polymerization, a fluoro(meth)acrylate, a fluorodiene, a fluorovinyl ether, a cyclic fluoromonomer, etc., may be mentioned, and from the viewpoint of compatibility, a fluoro(meth)acrylate is preferred.

As the fluoro(meth)acrylate, for example, those exemplified as compound (B) in WO2010/064609 may be mentioned, and the preferred modes may also be the same.

As the compound (C) having no fluorine atom, wherein the polymerizable functional group is a group capable of radical polymerization, a monofunctional (meth)acrylate, a polyfunctional (meth)acrylate, a (meth)acrylamide and derivatives thereof, an urethane acrylate, etc. may be mentioned.

As the monofunctional (meth)acrylate, for example, those exemplified as compound (C) in WO2010/064609 may be mentioned, and the preferred modes may also be the same.

As the polyfunctional (meth)acrylate, for example, those exemplified as compound (F) in WO2010/064609 may be mentioned, and the preferred modes may also be the same.

As the urethane acrylate, UA-160TM, UA-4200, U-4HA, UA-122P, manufactured by Shin-Nakamura Chemical Co., Ltd., UA-510H, UA-306I, UA-306T, UA-306H, AH-600, manufactured by Kyoeisha Chemical Co., Ltd., diurethane di(meth)acrylate, etc. may be mentioned.

As the compound (C), one type may be used alone, or two or more types may be used in combination.

(Additives)

The additives include surface active agents, antioxidants (heat stabilizers), thixotropic agents, antifoaming agents, light stabilizers, anti-gelling agents, photosensitizers, resins, metal oxide fine particles, carbon compounds, metallic fine particles, silane coupling agents, other organic compounds, etc.

(Content Proportion of Each Component in Curable Composition)

The proportion of the compound (A) is preferably at least 50 mass %, more preferably at least 60 mass %, further preferably at least 70 mass %, based on the curable composition. When the proportion of the compound (A) is at least the lower limit value in the above range, the effect by the compound (A) can be sufficiently exhibited. The upper limit value for the proportion of the compound (A) is preferably 99.9 mass %, more preferably 99 mass %.

The proportion of the polymerization initiator is preferably from 0.1 to 10 mass %, more preferably from 1 to 5 mass %, based on the curable composition. When the proportion of the polymerization initiator is at least the lower limit value in the above range, a cured product can be easily formed. When the proportion of the polymerization initiator is at most the upper limit value in the above range, it is possible to uniformly mix it, and therefore, the polymerization initiator remaining in the cured product will be less, and deterioration of physical properties of the cured product can be suppressed.

The proportion of the compound (C) is preferably from 0 to 49.9 mass %, more preferably from 0 to 30 mass %, based on the curable composition. When the proportion of the compound (C) is at most the upper limit value in the above range, the effect by the compound (A) can be sufficiently exhibited.

The proportion of additives is preferably from 0 to 10 mass %, more preferably from 0 to 5 mass %, in 100 mass % of the curable composition. When the proportion of the additives is at most the upper limit value in the above range, the curable composition can be uniformly mixed, and a homogeneous curable composition can be obtained.

In a case where the curable composition of the present invention is to be used for coating or the like, a solvent may be added to the curable composition of the present invention to obtain a coating composition. Here, the curable composition of the present invention is meant for a composition which does not substantially contain a solvent.

In the case of using the coating composition, the coating composition is applied to a substrate or the like to form a coating film made of the coating composition, and then, the solvent is removed from the coating film to form a film of the curable composition of the present invention, whereupon the film of the curable composition of the present invention is cured.

As the solvent, any solvent may be used so long as it is capable of dissolving the compound (A) and the polymerization initiator, and a solvent having at least one of an ester structure, a ketone structure, a hydroxy group and an ether structure, is preferred.

In the case of using the coating composition in the present invention, the amount of the solvent to be added to the curable composition, may be suitably adjusted depending on the desired viscosity, the coating properties, the desired film thickness, etc.

(Advantageous Effects)

The curable composition of the present invention as described above, contains a compound (A) having a structure of —$OCH_2CF_2CF_2CF_2OCFHCF_2$—, whereby it is possible, by curing the curable composition, to obtain a cured product which is excellent in heat resistance and mold release and has a high Abbe number.

<Cured Product>

The cured product of the present invention is one made by curing the curable composition of the present invention. The cured product of the present invention may be formed on the surface of a substrate, to obtain a laminate having a layer made of the cured product of the present invention and a layer made of the substrate.

The refractive index of the cured product to light having a wavelength of 589 nm is preferably at most 1.45, more preferably at most 1.43. When the refractive index is at most the upper limit value in the above range, reflection at the interface between the cured product and the air can be sufficiently reduced. The lower limit value of the refractive index of the cured product to light having a wavelength of 589 nm is 1.35.

The Abbe number of the cured product obtained from the above formula (I) is preferably at least 55, more preferably at least 60. When the Abbe number is at least the lower limit value in the above range, in the case of using it in combination with a glass substrate, chromatic aberration is less likely to occur. The higher the Abbe number, the better, and the upper limit value is not particularly limited, but is about 70 when considering that it is an organic substance.

(Method for Producing Cured Product)

The method for producing a cured product of the present invention may be a method of curing the curable composition in such a state that a mold having a reverse pattern of the fine pattern on its surface is in contact with the curable composition, to form a cured product having the fine pattern on its surface.

The curing method may be photocuring or thermosetting and may be suitably selected for use depending on the polymerization initiator. As the curing method, from the viewpoint of production efficiency of a cured product, photocuring is preferred.

(Advantageous Effects)

The cured product of the present invention as described above, is one obtained by curing a curable composition containing the compound (A) having the structure of —$OCH_2CF_2CF_2CF_2OCFHCF_2$—, whereby it is excellent in heat resistance and mold-mold release and has a high Abbe number.

EXAMPLES

Now, the present invention will be described in detail with reference to Examples, but the present invention is not limited thereto.

Ex. 1 to 7 are Examples of the present invention, and Ex. 8 to 10 are Comparative Examples.

(Viscosity of Compound)

The viscosity of a compound such as the compound (A) was obtained by measuring the dynamic viscoelasticity at a shear rate of 10 s$^{-1}$ at 25° C. by means of a dynamic viscoelasticity measuring apparatus (Physica MCR301, manufactured by Anton Paar Co.).

(Refractive Index of Compound)

The refractive index of a compound such as the compound (A) was measured by using an Abbe refractometer (Multi-Wavelength Abbe Refractometer: DR-M2, manufactured by Atago Co., Ltd.) at a temperature of 25° C. at a wavelength of 589 nm.

(Abbe Number of Compound)

The Abbe number of a compound such as the compound (A) was calculated from the following formula (I) by measuring the respective refractive indices at wave lengths of 589 nm, 486 nm and 656 nm at a temperature of 25° C. by using the Abbe refractometer (the same as mentioned above).

$$v_D = (n_D - 1)/(n_F - n_C) \qquad (I)$$

where $v_D$ is the Abbe number, $n_D$ is the refractive index to light with a wavelength of 589 nm, $n_F$ is the refractive index to light with a wavelength of 486 nm, and $n_C$ is the refractive index to light with a wavelength of 656 nm.

(Refractive Index of Cured Product)

A curable composition was applied to the surface of a silicon wafer and irradiated with ultraviolet rays from a high pressure mercury lamp with an exposure amount of 1,000 mJ/cm$^2$ to form a film-form cured product. Using a refractive index measuring apparatus (prism coupler: 2010/M, manufactured by US Metricon Corporation), the refractive indices of the film-form cured product to lights with wavelengths of 473 nm, 594 nm and 658 nm, were measured, and the refractive index to light with a wavelength of 589 nm was calculated by using Metricon Fit attached to the apparatus.

(Abbe Number of Cured Product)

Using Metricon Fit attached to the above-mentioned apparatus, the refractive indices at the respective wavelengths were calculated, and from the above equation (I), the Abbe number was calculated.

(Heat Resistance of Cured Product)

The curable composition was applied to the surface of a glass substrate and irradiated with ultraviolet rays from a high pressure mercury lamp with an exposure amount of 3,000 mJ/cm$^2$, to form a film-form cured product thus to obtain a sample. The transmittance of the sample to light with a wavelength of 450 nm was measured by using a ultraviolet/visible/near-infrared spectrophotometer (Solid Spec-3700, manufactured by Shimadzu Corporation). The sample was heated at 125° C. for 800 hours in an air atmosphere. The transmittance of the sample to light with a wavelength of 450 nm after heating was measured by using the ultraviolet/visible/near-infrared spectrophotometer (same as mentioned above). The change rate in transmittance was obtained from the following formula (II).

Change rate in transmittance (%)=(transmittance before heating−transmittance after heating)/transmittance before heating×100    (II)

The heat resistance of a cured product was evaluated by the following standards.

○ (good): The change rate in transmittance is less than 15%.

x (bad): The change rate in transmittance is at least 15%.

(Releasability of Cured Product)

A curable composition was sandwiched between two glass substrates and cured by irradiation with ultraviolet rays from a high pressure mercury lamp with an exposure amount of 3,000 mJ/cm$^2$. The mold release at the time of peeling off the glass substrates from the cured product was evaluated by the following standards.

○ (good): The glass substrates were easily peeled off from the cured product.

x (bad): It was difficult to peel off the glass substrates from the cured product, or cohesive failure occurred in the cured product.

(Water Contact Angle of Cured Product)

Using a contact angle meter (portable contact angle meter PCA-1, manufactured by Kyowa Interface Science Co., LTD.), the contact angle of pure water was measured 4 times, whereupon an arithmetic mean value was obtained, and this value was adopted as the water contact angle. The water contact angle of the cured product becomes an index for mold release of the cured product, but needless to say, only by this value, the mold release may not be judged.

Ex. 1

Step (i):

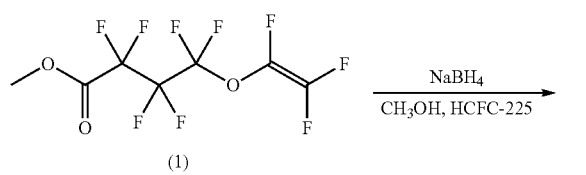

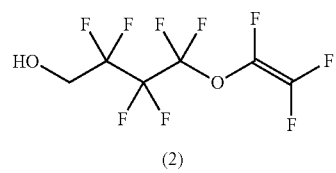

Into a 500 mL three-necked flask, 16.5 g of sodium borohydride and 200 g of HCFC-225 (ASAHIKLIN (registered trademark) AK-225, manufactured by Asahi Glass Company, Limited) were added and stirred in an ice bath. To this, a mixture of 200 g of a compound (1) (manufactured by Asahi Glass Company, Limited) and 27.2 g of methanol, was slowly dropwise added so that the internal temperature would not exceed 15° C. After dropwise addition of the total amount, the mixture was stirred for 2 hours while immersed in an ice bath. 250 mL of 2N HCl was introduced to terminate the reaction. The reaction solution was washed three times with water and a saturated sodium chloride aqueous solution. After drying over sodium sulfate, the solid was removed by filtration, and the solvent was removed by distillation under reduced pressure, to obtain a compound (2) as a colorless transparent liquid. The yield was 168 g (yield: 92%). The product was analyzed by gas chromatography, whereby the compound (2) formed was in a purity of 98.7%, and no unreacted compound (1) was detected. Without purification, this product was subjected to the next step (ii).

Step (ii):

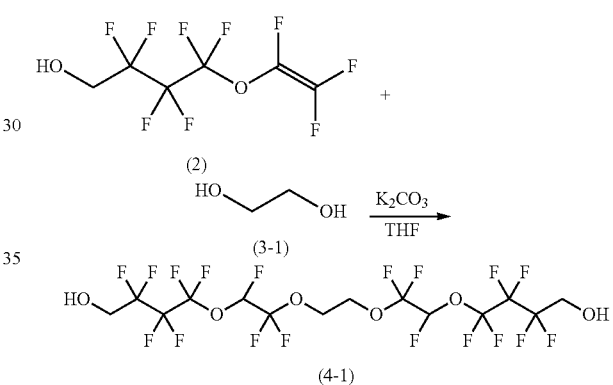

Into a 500 mL three-necked flask, 15 g of ethylene glycol (compound (3-1)), 73 g of potassium carbonate and 200 mL of tetrahydrofuran (THF) were added, and nitrogen gas was blown into the reaction system to bring it to an inert atmosphere. With stirring at 60° C., 134 g of the compound (2) was gradually dropwise added thereto. After dropwise addition of the total amount, the mixture was stirred at 60° C. for 8 hours. After confirming that the raw material had been consumed by thin layer chromatography (TLC), the reaction solution was neutralized by adding 1N hydrochloric acid until the reaction solution became transparent, to terminate the reaction. After washing the reaction solution twice with HCFC-225, HCFC-225 was recovered, and the reaction solution was further washed with a saturated sodium chloride aqueous solution. After drying over sodium sulfate, the solid was removed by filtration, and the solvent was distilled off under reduced pressure, followed by purification by column chromatography to obtain a compound (4-1) as a colorless transparent liquid. The yield was 108 g (yield: 72.3%). This product was subjected to the next step (iii).

NMR spectrum of compound (4-1);

$^1$H-NMR (300 MHz, solvent: CD$_3$COCD$_3$, standard: TMS) δ (ppm): 3.54, 3.65, 3.85, 5.54.

Step (iii):

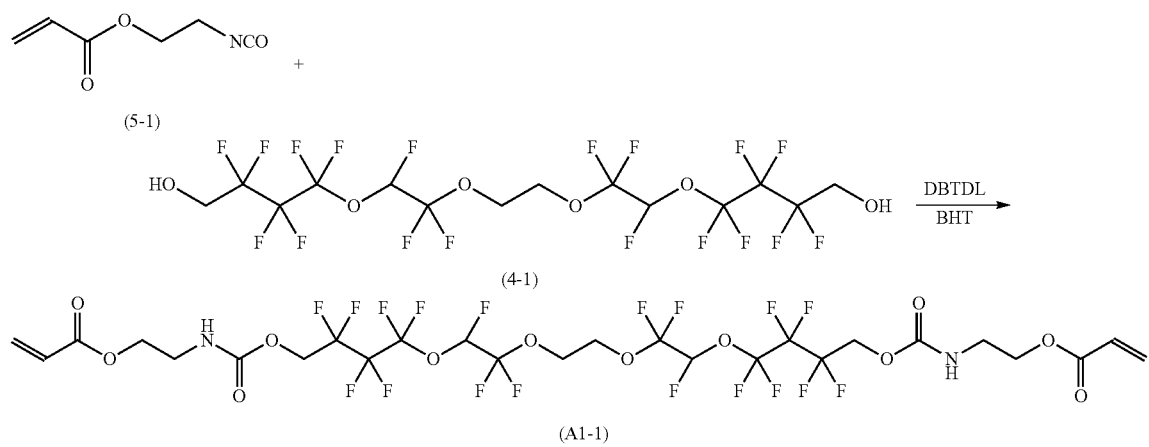

Into a 200 mL three-necked flask, 60 g of the compound (4-1) was charged, and under reduced pressure, while stirring, the temperature was raised to 90° C., followed by dehydration for 3 hours. The pressure was returned to normal pressure, the temperature was lowered to 50° C., 0.17 g of dibutylhydroxytoluene (BHT) and 30 g of a compound (5-1) (Karenz (registered trademark) AOI, manufactured by Showa Denko K.K.) were added, the temperature was raised to 60° C., followed by a reaction for 1 hour, and 0.006 g of dibutyltin dilaurate (DBTDL) was added and stirred for 6 hours. The completion of the reaction was judged by disappearance of a peak (in the vicinity of 2,250 cm$^{-1}$) attributable to isocyanate by FT-IR-1. The reaction solution was purified by column chromatography to obtain a compound (A1-1) as a colorless transparent liquid. The yield was 60.4 g (yield: 69.1%). The evaluation results are shown in Table 1.

NMR Spectrum of Compound (A1-1);
$^1$H-NMR (300 MHz, solvent: CDCl$_3$, standard: TMS) δ (ppm): 3.15, 3.54, 4.58, 4.66, 5.54, 5.69, 6.05, 6.27, 8.03.

Curable Composition:

10 g of the compound (A1-1) and 0.3 g of a photopolymerization initiator (IRGACURE (registered trademark) 184, manufactured by BASF Corp.) were mixed to obtain a curable composition in Ex. 1. The evaluation results are shown in Table 2.

Ex. 2

Step (iii):

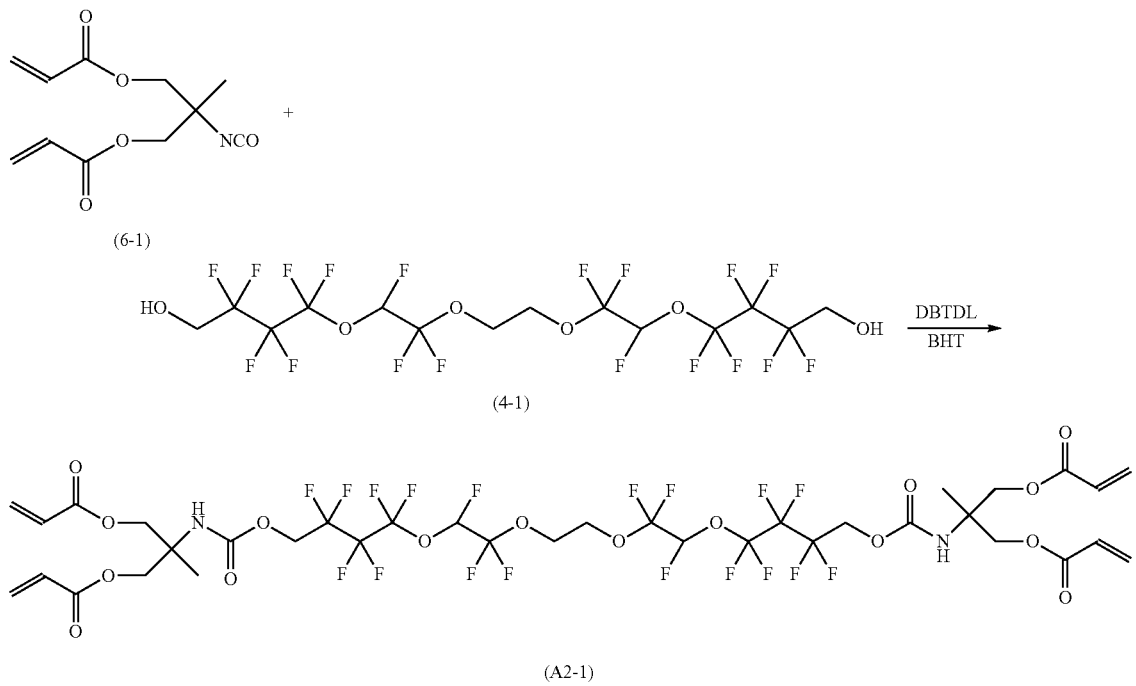

A compound (A2-1) was obtained in the same manner as in step (iii) in Ex. 1 except that instead of 30 g of the compound (5-1), 51 g of a compound (6-1) (Karenz (registered trademark) BEI, manufactured by Showa Denko K.K.) was used. The yield was 88.4 g (yield: 83.1%). The evaluation results are shown in Table 1.

NMR Spectrum of Compound (A2-1);

$^1$H-NMR (300 MHz, solvent: CDCl$_3$, standard: TMS) δ (ppm): 1.57, 3.54, 4.66, 4.71, 5.54, 5.69, 6.05, 6.27, 8.03.

Curable Composition:

A curable composition in Ex. 2 was obtained in the same manner as in Ex. 1 except that instead of the compound (A1-1), the compound (A2-1) was used. The evaluation results are shown in Table 2.

Ex. 3

Step (ii):

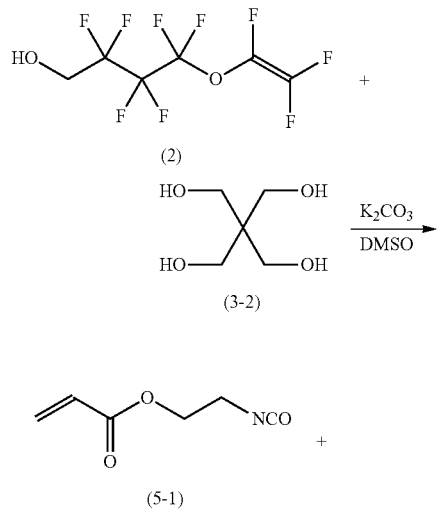

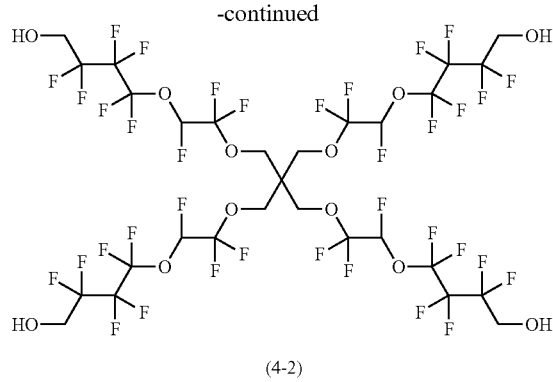

(4-2)

Into a 500 mL three-necked flask, 15 g of pentaerythritol (compound (3-2)), 67 g of potassium carbonate and 200 mL of dimethyl sulfoxide (DMSO) were added, and nitrogen gas was blown into the reaction system to bring it to an inert atmosphere. While stirring at 60° C., 123 g of the compound (2) was gradually dropwise added thereto. After dropwise addition of the total amount, the mixture was stirred at 60° C. for 8 hours. After confirming by TLC that the raw material had been consumed, the reaction solution was neutralized by adding 1N hydrochloric acid until the reaction solution became transparent, and the reaction was terminated. The reaction solution was washed twice with HCFC-225, and then the HCFC-225 layer was recovered and further washed with a saturated sodium chloride aqueous solution. After drying over sodium sulfate, the solid was removed by filtration, and the solvent was distilled off under reduced pressure, followed by purification by column chromatography to obtain a compound (4-2) as a colorless transparent liquid. The yield was 63.7 g (yield: 46.3%). This product was subjected to the next step (iii).

Step (iii):

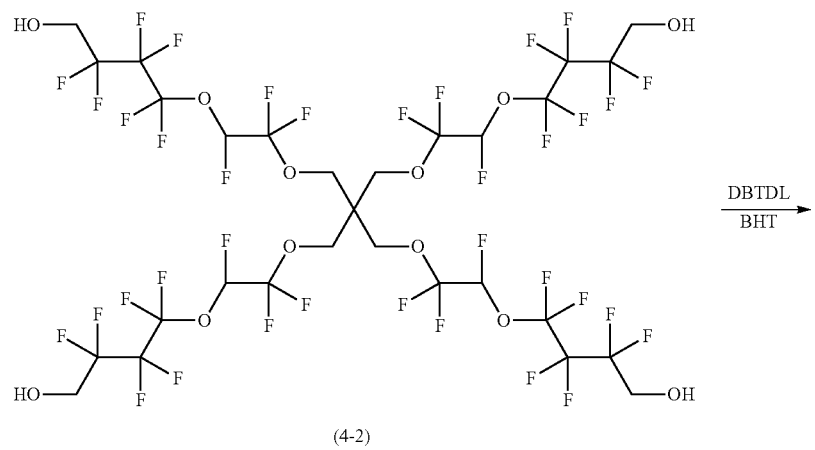

(4-2)

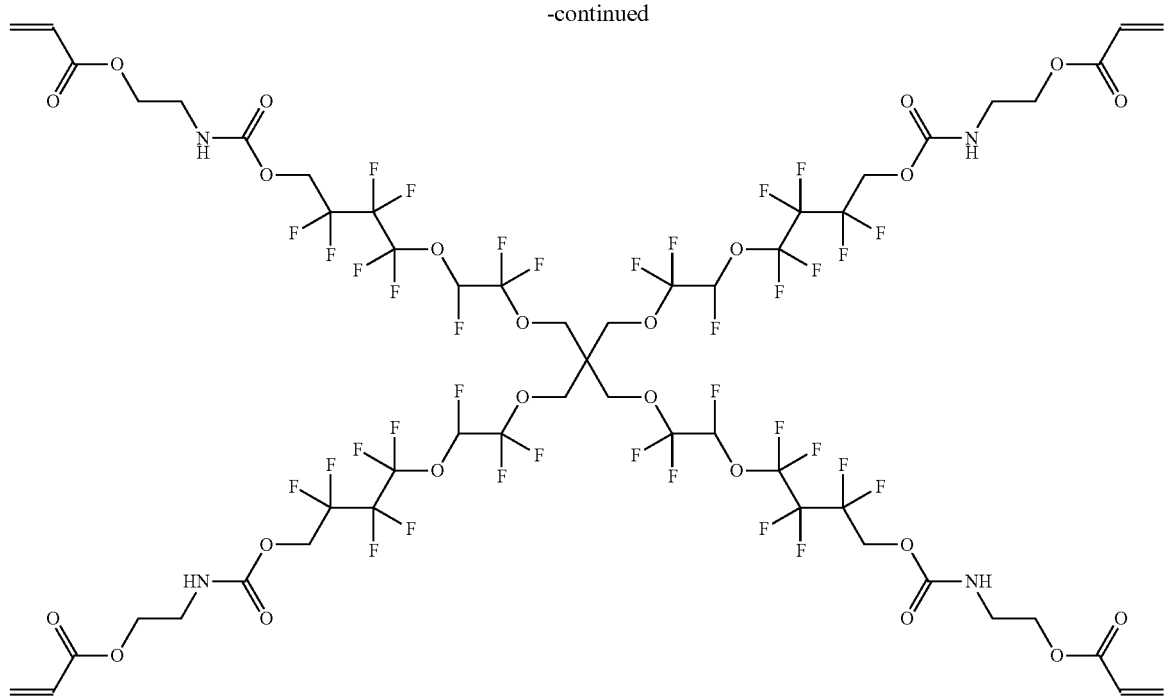

(A1-2)

Into a 200 mL three-necked flask, 60 g of the compound (4-2) was charged, and under reduced pressure, while stirring, the temperature was raised to 90° C., followed by dehydration for 3 hours. The pressure was returned to normal pressure, the temperature was lowered to 50° C., 0.17 g of BHT and 27 g of a compound (5-1) were added, the temperature was raised to 60° C., followed by a reaction for one hour, and 0.006 g of DBTDL was added, followed by stirring. The completion of the reaction was judged by disappearance of a peak (2,250 cm$^{-1}$) attributable to isocyanate by FT-IR. The reaction solution was purified by column chromatography to obtain a compound (A1-2) as a colorless transparent liquid. The yield was 67.1 g (yield: 77.1%). The evaluation results are shown in Table 1.

NMR Spectrum of Compound (A1-2);
$^1$H-NMR (300 MHz, solvent: CDCl$_3$, standard: TMS) δ (ppm): 3.24, 3.27, 4.41, 5.54, 5.69, 6.05, 6.27, 8.23.

Curable Composition:

A curable composition in Ex. 3 was obtained in the same manner as in Ex. 1 except that instead of the compound (A1-1), the compound (A1-2) was used. The evaluation results are shown in Table 2.

Ex. 4

Step (iii):

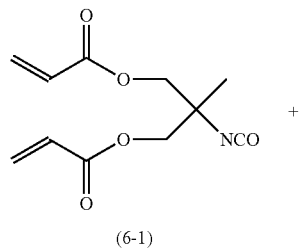

(6-1)

-continued

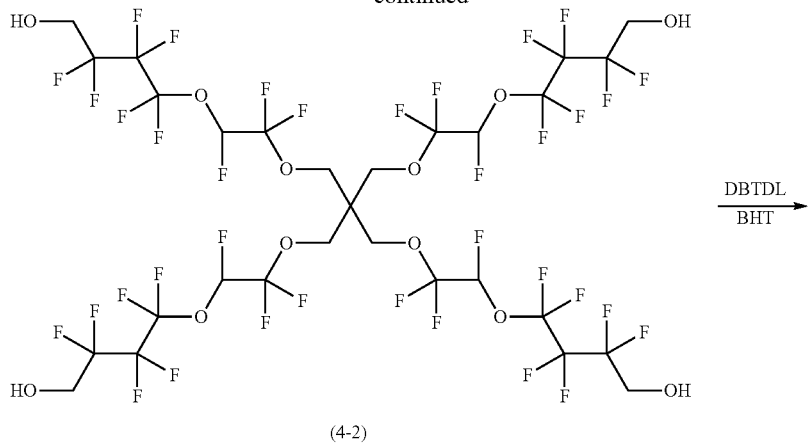

(4-2)

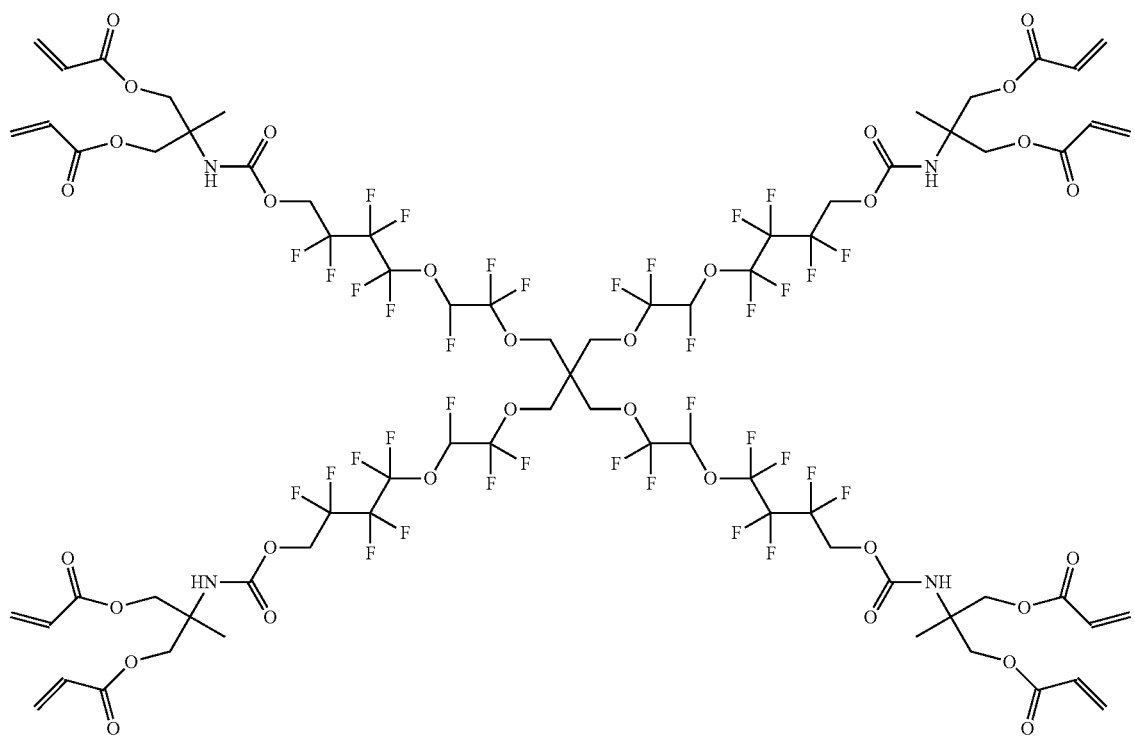

(A2-2)

A compound (A2-2) was obtained in the same manner as in step (iii) in Ex. 3 except that instead 27 g of compound (5-1), 51 g of the compound (6-1) was used. The yield was 50.4 g (yield: 47.5%). The evaluation results are shown in Table 1.

NMR Spectrum of Compound (A2-2);
$^1$H-NMR (300 MHz, solvent: CDCl$_3$, standard: TMS) δ (ppm): 1.39, 3.27, 4.33, 4.40, 5.54, 5.69, 6.05, 6.27, 8.25.

Curable Composition:

A curable composition in Ex. 4 was obtained in the same manner as in Ex. 1 except that instead of the compound (A1-1), the compound (A2-2) was used. The evaluation results are shown in Table 2.

Ex. 5

Step (ii):

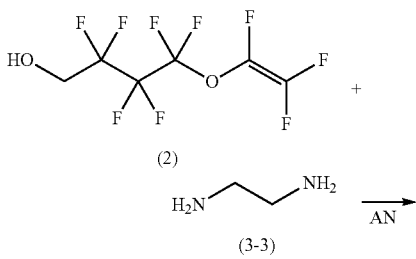

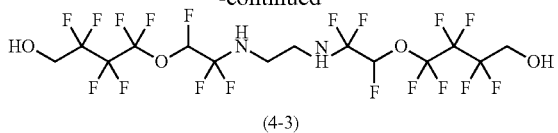

(4-3)

Into a 200 mL three-necked flask, 1.1 g of ethylenediamine (compound (3-3)) and 50 mL of acetonitrile (AN) were added, and nitrogen gas was blown into the reaction system to bring it to an inert atmosphere. To this, 10.0 g of the compound (2) was slowly dropwise added. After dropwise addition of the total amount, the mixture was stirred at 60° C. for 8 hours. After confirming by TLC that the raw material had been consumed, the reaction solution was neutralized by adding 1N hydrochloric acid until the reaction solution became transparent, and the reaction was terminated. The reaction solution was washed twice with HCFC-225, and then, HCFC-225 layer was recovered and further washed with a saturated sodium chloride aqueous solution. After drying over sodium sulfate, the solid was removed by filtration, and the solvent was distilled off under reduced pressure, followed by purification by column chromatography to obtain a compound (4-3) as a colorless transparent liquid. The yield was 4.5 g (yield: 43%). This product was subjected to the next step (iii).

Step (iii):

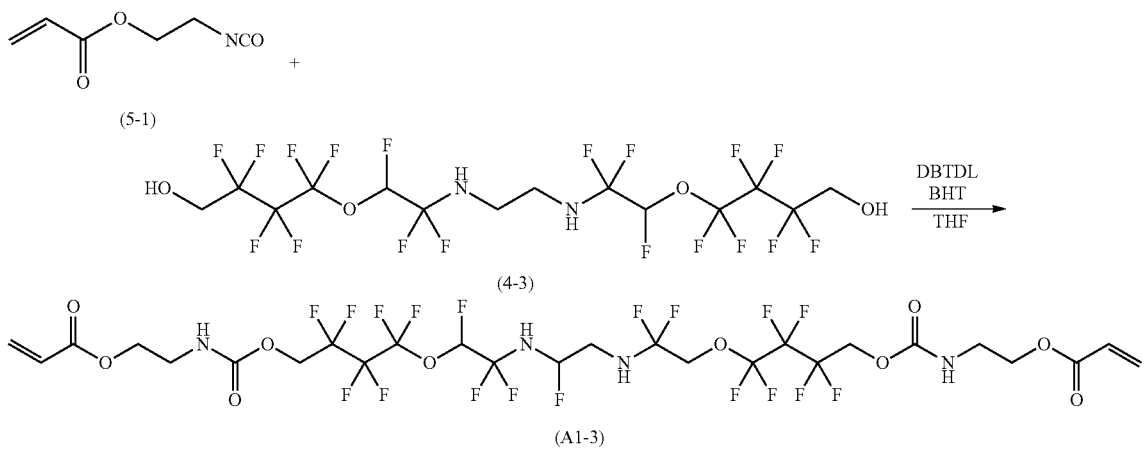

(A1-3)

Into a 50 mL three-necked flask, 2 g of the compound (4-3), 6 mg of BHT, 2 mg of DBTDL, 1.1 g of a compound (5-1) and 20 mL of THF were added and stirred at room temperature for 12 hours. The completion of the reaction was judged by disappearance of a peak (2,250 cm$^{-1}$) attributable to isocyanate by FT-IR. The reaction solution was purified by column chromatography to obtain a compound (A1-3) as a colorless transparent liquid. The yield was 2.5 g (yield: 85%). The evaluation results are shown in Table 1.

NMR Spectrum of Compound (A1-3);

$^1$H-NMR (300 MHz, solvent: Acetone-d6, standard: TMS) δ (ppm): 3.51, 4.24, 4.71, 5.89, 6.14, 6.35, 6.46, 7.03, 8.23.

Curable Composition:

A curable composition in Ex. 5 was obtained in the same manner as in Ex. 1 except that instead of the compound (A1-1), the compound (A1-3) was used. The evaluation results are shown in Table 2.

Ex. 6

Step (ii):

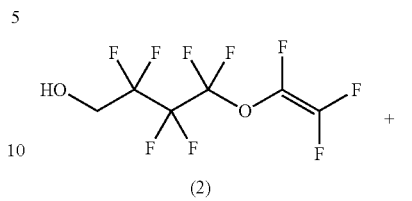

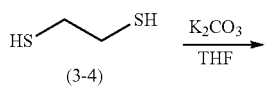

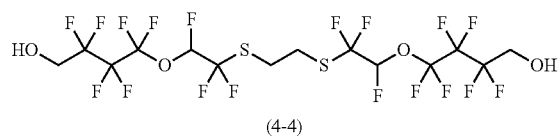

(4-4)

Into a 200 mL three-necked flask, 0.94 g of 1,2-ethanedithiol (compound (3-4)), 4.1 g of potassium carbonate and 30 mL of tetrahydrofuran were added, and nitrogen gas was blown into the reaction system to bring it to an inert atmosphere. To this, 5.6 g of the compound (2) was slowly dropwise added. After dropwise addition of the total amount, the mixture was stirred at 60° C. for 8 hours. After confirming by TLC that the raw material had been consumed, the reaction solution was neutralized by adding 1N hydrochloric acid until the reaction solution became transparent, and the reaction was terminated. The reaction solution was washed twice with HCFC-225, and then HCFC-225 layer was recovered and further washed with a saturated sodium chloride aqueous solution. After drying over sodium sulfate, the solid was removed by filtration, and the solvent was distilled off under reduced pressure, followed by purification by column chromatography to obtain a compound (4-4) as a colorless transparent liquid. The yield was 4.0 g (yield: 61%). This product was subjected to the next step (iii).

Step (iii):

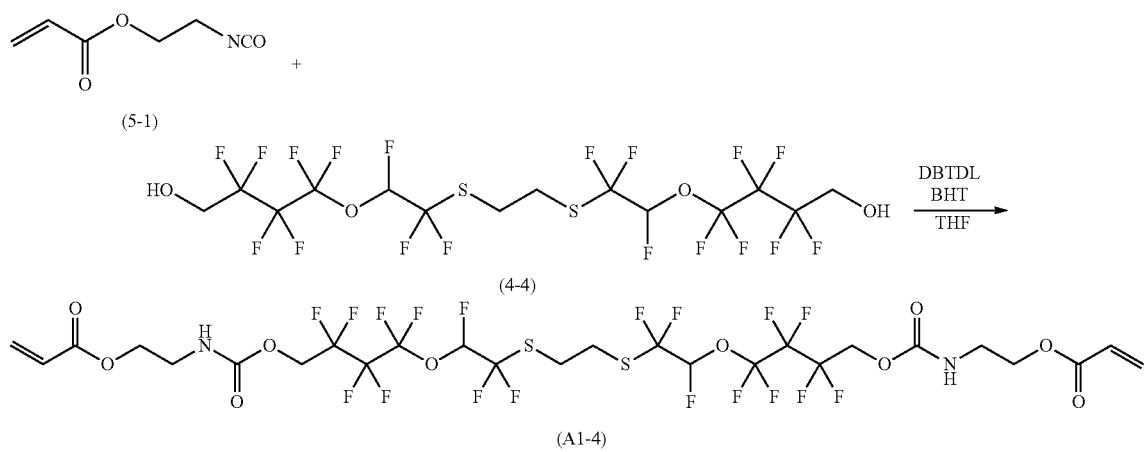

Into a 50 mL three-necked flask, 2 g of the compound (4-4), 6 mg of BHT, 2 mg of DBTDL, 1.2 g of a compound (5-1) and 20 mL of THF were added and stirred at room temperature for 12 hours. The completion of the reaction was judged by disappearance of a peak (2,250 cm$^{-1}$) attributable to isocyanate by FT-IR. The reaction solution was purified by column chromatography to obtain a compound (A1-4) as a colorless transparent liquid. The yield was 2.5 g (yield: 85%). The evaluation results are shown in Table 1.

NMR Spectrum of Compound (A1-4);
$^1$H-NMR (300 MHz, solvent: CDCl$_3$, standard: TMS) δ (ppm): 3.18, 3.50, 4.25, 5.86, 6.10, 6.41.

Curable Composition:

A curable composition in Ex. 6 was obtained in the same manner as in Ex. 1 except that instead of the compound (A1-1), the compound (A4-1) was used. The evaluation results are shown in Table 2.

Ex. 7

Step (iii):

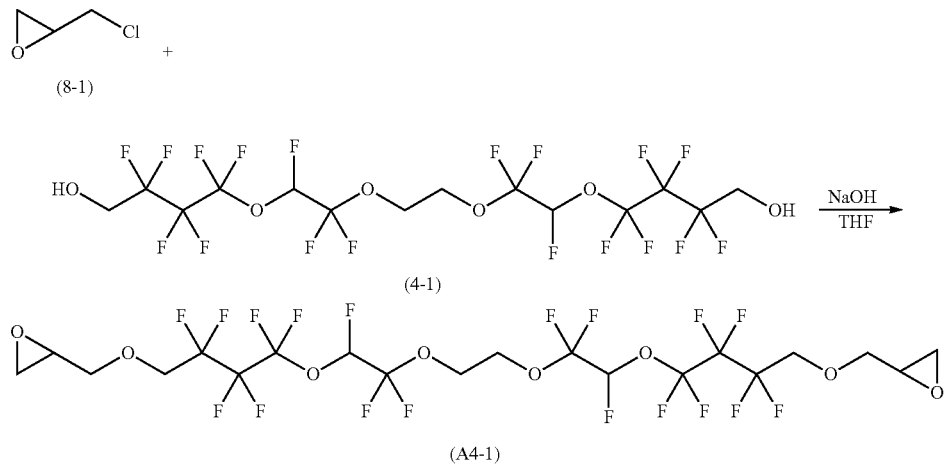

Into a 50 mL three-necked flask (4-1), 2 g of the compound (4-1), 0.57 g of finely pulverized sodium hydroxide and 25 mL of THF were added, and nitrogen gas was blown into the reaction system to bring it to an inert atmosphere. To this, 1.27 g of epichlorohydrin (8-1) was slowly dropwise added. After dropwise addition of the total amount, the mixture was stirred at 50° C. for 6 hours. After returning the reaction solution to room temperature, 25 mL of HCFC-225 and 25 mL of a saturated ammonium chloride aqueous solution were added, and the HCFC-225 layer was extracted and washed with a saturated sodium chloride aqueous solution, followed by purification by column chromatography to obtain a compound (A4-1) as a colorless transparent liquid. The yield was 2.0 g (yield: 56%).

NMR Spectrum of Compound (A4-1);
$^1$H-NMR (300 MHz, solvent: Acetone-d6, standard: TMS) δ (ppm): 2.54, 2.72, 3.10, 3.44, 3.95, 4.06, 4.28, 6.39.

Curable Composition:

A curable composition in Ex. 7 was obtained in the same manner as in Ex. 1 except that instead of the compound (A1-1), the compound (A4-1) was used, and as the photopolymerization initiator, CPI-210S (manufactured by San-Apro Ltd.) was used. The evaluation results are shown in Table 2.

Ex. 8

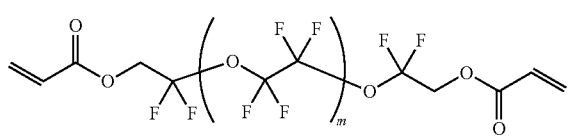
(C-1)

A compound (C-1) (NK Ester DA-F4EO, manufactured by Shin-Nakamura Chemical Corporation, m=2) was prepared. The evaluation results are shown in Table 1.

A curable composition in Ex. 8 was obtained in the same manner as in Ex. 1 except that instead of the compound (A1-1), the compound (C-1) was used. The evaluation results are shown in Table 2.

Ex. 9

As a compound (C-2), a urethane acrylate with a polyether skeleton (NK Oligo UA-160TM, manufactured by Shin-Nakamura Chemical Corporation) was prepared. The evaluation results are shown in Table 1.

A curable composition in Ex. 9 was obtained in the same manner as in Ex. 1 except that instead of the compound (A1-1), the compound (C-2) was used. The evaluation results are shown in Table 2.

Ex. 10

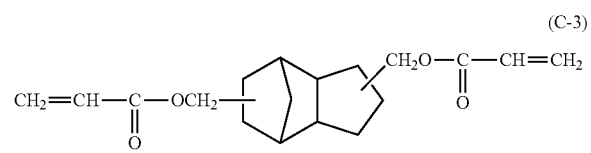
(C-3)

A compound (C-3) (NK Ester A-DCP, manufactured by Shin-Nakamura Chemical Corporation) was prepared. The evaluation results are shown in Table 1.

A curable composition in Ex. 10 was obtained in the same manner as in Ex. 1 except that instead of the compound (A1-1), the compound (C-3) was used. The evaluation results are shown in Table 2.

TABLE 1

|  | Compound | Fluorine content [mass %] | Viscosity [mPa · s] | Refractive index 589 nm | Abbe number ν D |
|---|---|---|---|---|---|
| Ex. 1 | (A1-1) | 38.0 | 1,900 | 1.3898 | 60.9 |
| Ex. 2 | (A2-1) | 31.2 | 1,800 | 1.4180 | 62.4 |
| Ex. 3 | (A1-2) | 37.7 | 1,400 | 1.3916 | 64.2 |
| Ex. 4 | (A2-2) | 31.0 | 1,700 | 1.4298 | 60.5 |
| Ex. 5 | (A1-3) | 37.4 | 1,400 | 1.4155 | 56.1 |
| Ex. 6 | (A1-4) | 36.0 | 1,200 | 1.4294 | 53.0 |
| Ex. 7 | (A4-1) | 45.8 | 50 | 1.3687 | 73.7 |
| Ex. 8 | (C-1) | 44.0 | 12 | 1.3558 | 61.3 |
| Ex. 9 | (C-2) | 0 | 110,000 | 1.4819 | 54.1 |
| Ex. 10 | (C-3) | 0 | 120 | 1.5102 | 47.9 |

TABLE 2

| | Cured product | | | | |
|---|---|---|---|---|---|
| | Refractive index 589 nm | Abbe number ν D | Heat resistance | Releasability | Water contact angle [°] |
| Ex. 1 | 1.4086 | 62.9 | ○ | ○ | 83.2 |
| Ex. 2 | 1.4426 | 58.4 | ○ | ○ | 81.4 |
| Ex. 3 | 1.4176 | 61.1 | ○ | ○ | 82.5 |
| Ex. 4 | 1.4500 | 65.8 | ○ | ○ | 80.9 |
| Ex. 5 | 1.4483 | 57.7 | ○ | ○ | 78.3 |
| Ex. 6 | 1.4530 | 55.1 | ○ | ○ | 83.5 |
| Ex. 7 | 1.3914 | 71.2 | ○ | ○ | 80.2 |
| Ex. 8 | 1.3900 | 62.6 | x | ○ | 91.4 |
| Ex. 9 | 1.4894 | 55.1 | x | x | 75.0 |
| Ex. 10 | 1.5336 | 52.4 | x | ○ | 68.6 |

The cured product made from the curable composition containing a compound (A), in each of Ex. 1 to 7, was excellent in heat resistance and mold release and had a high Abbe number.

The cured product made from the curable composition containing a fluorinated compound other than a compound (A), in Ex. 8 (A), was inferior in heat resistance, although it was excellent in mold release and had a high Abbe number.

The cured product made from the curable composition containing a non-fluorinated urethane oligomer, in Ex. 9, was inferior in heat resistance and mold release and had a low Abbe number.

The cured product made from the curable composition containing a non-fluorinated compound having a polycyclic skeleton, in Ex. 10, was inferior in heat resistance and had a low Abbe number, although it was excellent in mold release.

INDUSTRIAL APPLICABILITY

The fluorinated compound of the present invention is useful as a material for a curable composition to be used for the production of optical members (such as lens arrays, prisms, anti-reflection films, etc.), recording media, semiconductor devices, etc.

What is claimed is:

1. A fluorinated compound represented by the following formula (A):

$$[Z-OCH_2CF_2CF_2CF_2OCFHCF_2-X-]_nQ \qquad (A)$$

where n is an integer of from 2 to 6, Q is a n-valent organic group, X is —O—, —NH— or —S—, and Z is a group having at least one polymerizable functional group.

2. The fluorinated compound according to claim 1, wherein Q is a n-valent hydrocarbon group, or a group having at least one etheric oxygen atom between carbon atoms in an n-valent hydrocarbon group.

3. The fluorinated compound according to claim 2, wherein the number of carbon atoms in Q is from 2 to 24, and in a case where Q has etheric oxygen atom(s) between carbon atoms, the number of such etheric oxygen atom(s) is 1 or 2.

4. The fluorinated compound according to claim 1, wherein X is —O—.

5. The fluorinated compound according to claim 1, wherein the polymerizable functional group is a group having a polymerizable carbon-carbon double bond, or an epoxy group.

6. The fluorinated compound according to claim 5, wherein the group having a polymerizable carbon-carbon double bond is a (meth)acryloyl group.

7. The fluorinated compound according to claim 1, wherein Z has —NHC(O)— at the end on the side bonded to the oxygen atom adjacent to Z (provided that the carbon atom in the —NHC(O)— is bonded to the oxygen atom adjacent to Z).

8. The fluorinated compound according to claim 1, wherein Z is a group represented by the following formula (g1), a group represented by the following formula (g2), a group represented by the following formula (g3) or a group represented by the following formula (g4):

$$CH_2\!=\!C(R)\!-\!C(O)O\!-\!R^1\!-\!NHC(O)\!- \quad (g1)$$

$$\{CH_2\!=\!C(R)\!-\!C(O)O\!-\!\}_2R^2\!-\!NHC(O)\!- \quad (g2)$$

$$CH_2\!=\!C(R)\!-\!C(O)O\!-\!R^3\!-\!CH(OH)\!-\!CH_2\!- \quad (g3)$$

$$Ep\text{-}R^4\!- \quad (g4)$$

where R is a hydrogen atom or a methyl group, $R^1$ is a $C_{1-6}$ alkylene group, or a group having at least one etheric oxygen atom between carbon atoms in a $C_{2-6}$ alkylene group, $R^2$ is a $C_{1-4}$ alkanetriyl group, or a group having at least one etheric oxygen atom between carbon atoms in a $C_{2-4}$ alkanetriyl group, $R^3$ is a $C_{1-5}$ alkylene group, or a group having at least one etheric oxygen atom between carbon atoms in a $C_{2-5}$ alkylene group, $R^4$ is a $C_{1-5}$ alkylene group, or a group having at least one etheric oxygen atom between carbon atoms in a $C_{2-5}$ alkylene group, and Ep is an epoxy group.

9. A curable composition comprising at least one fluorinated compound as defined in claim 1, and a polymerization initiator.

10. The curable composition according to claim 9, which further contains a compound having at least one polymerizable functional group, but excluding the fluorinated compound.

11. The curable composition according to claim 9, wherein the polymerization initiator is a photopolymerization initiator.

12. A cured product obtained by curing the curable composition as defined in claim 9.

* * * * *